United States Patent
Orr et al.

(10) Patent No.: US 9,907,511 B2
(45) Date of Patent: Mar. 6, 2018

(54) SYSTEM AND METHOD OF IDENTIFYING BREATHS BASED SOLELY ON CAPNOGRAPHIC INFORMATION

(75) Inventors: Joseph Allen Orr, Park City, UT (US); Lara Marie Brewer, Bountiful, UT (US)

(73) Assignee: Koninklijke Philips N.V., Eindhoven (NL)

( * ) Notice: Subject to any disclaimer, the term of this patent is extended or adjusted under 35 U.S.C. 154(b) by 1055 days.

(21) Appl. No.: 13/993,097

(22) PCT Filed: Dec. 5, 2011

(86) PCT No.: PCT/IB2011/055447
§ 371 (c)(1),
(2), (4) Date: Jun. 11, 2013

(87) PCT Pub. No.: WO2012/080896
PCT Pub. Date: Jun. 21, 2012

(65) Prior Publication Data
US 2013/0261488 A1    Oct. 3, 2013

Related U.S. Application Data

(60) Provisional application No. 61/424,117, filed on Dec. 17, 2010.

(51) Int. Cl.
*A61B 5/08* (2006.01)
*A61B 5/00* (2006.01)
*A61B 5/083* (2006.01)

(52) U.S. Cl.
CPC ............ *A61B 5/7278* (2013.01); *A61B 5/082* (2013.01); *A61B 5/0816* (2013.01); *A61B 5/0836* (2013.01)

(58) Field of Classification Search
None
See application file for complete search history.

(56) References Cited

U.S. PATENT DOCUMENTS

| | | | |
|---|---|---|---|
| 4,602,644 A * | 7/1986 | DiBenedetto | A61B 5/087 128/207.18 |
| 6,828,910 B2 | 12/2004 | Vanryzin et al. | |
| 7,034,692 B2 | 4/2006 | Hickle | |
| 7,371,220 B1 * | 5/2008 | Koh | A61B 5/0809 600/529 |
| 8,357,099 B2 | 1/2013 | Gunneson et al. | |

(Continued)

FOREIGN PATENT DOCUMENTS

| | | |
|---|---|---|
| JP | S61358 A | 1/1986 |
| WO | 2008122806 A1 | 10/2008 |

OTHER PUBLICATIONS

Dow, Douglas E., et al. "EMG-based detection of inspiration in the rat diaphragm muscle." 2006. Engineering in Medicine and Biology Society, 2006. EMBS'06. 28th Annual International Conference of the IEEE. pp. 1204-1207.*

(Continued)

*Primary Examiner* — Jacqueline Cheng
*Assistant Examiner* — Jairo Portillo (57) ABSTRACT

Breaths of a subject are identified based on the concentration of carbon dioxide at or near the airway of the subject. Troughs corresponding to inhalation are identified and plateaus corresponding to exhalation are identified. A breath is identified responsive to a trough being followed by a plateau.

20 Claims, 3 Drawing Sheets

(56) References Cited

U.S. PATENT DOCUMENTS

| | | | |
|---|---|---|---|
| 9,039,629 B2 | 5/2015 | Zhou et al. | |
| 9,655,543 B2 | 5/2017 | Aoki et al. | |
| 2002/0082511 A1* | 6/2002 | Carlebach | A61B 5/0836 |
| | | | 600/529 |
| 2002/0104536 A1* | 8/2002 | Richey, II | A61M 16/00 |
| | | | 128/204.22 |
| 2008/0009762 A1 | 1/2008 | Hampton et al. | |
| 2008/0097234 A1* | 4/2008 | Nicolazzi | A61B 5/087 |
| | | | 600/538 |
| 2008/0125665 A1* | 5/2008 | Nigam | A61B 5/04021 |
| | | | 600/509 |
| 2009/0050154 A1* | 2/2009 | Strothmann | A61M 16/00 |
| | | | 128/204.23 |
| 2009/0118632 A1 | 5/2009 | Goepp | |
| 2009/0299430 A1 | 12/2009 | Davies et al. | |
| 2010/0249630 A1* | 9/2010 | Droitcour | A61B 5/05 |
| | | | 600/529 |

OTHER PUBLICATIONS

Bao, W., et al. "Expert capnogram analysis." IEEE Engineering in Medicine and Biology Magazine 11.1 (1992): 62-66.*

* cited by examiner

SYSTEM AND METHOD OF IDENTIFYING BREATHS BASED SOLELY ON CAPNOGRAPHIC INFORMATION

BACKGROUND

1. Field of the Disclosure

The invention relates to the identification of breaths (e.g., for breath rate determination) based solely on the concentration of a gaseous molecular species, such as carbon dioxide, at or near the airway of a subject.

2. Description of the Related Art

Systems that monitor the concentration of carbon dioxide at or near the airway of a subject are known. In conventional systems, it may be difficult to accurately and/or precisely identify breaths based solely on this capnographic information. Typically, the concentration of level of carbon dioxide is monitored, and dips below an upper level corresponding to inhalations are counted as breaths. However, this technique is susceptible to counting false breaths caused by cardiogenic oscillations and other ineffective gas movements the breathing circuit.

Some conventional systems include additional sensors, such as flow and/or pressure sensors to enhance and/or facilitate identification of breaths. The addition of sensors to a system also increases the cost and/or is accompanied by other drawbacks.

SUMMARY

One aspect of this disclosure relates to a system configured to detect breaths based on capnographic information. In one embodiment, the system comprises a sensor and a processor. The sensor is configured to generate output signals conveying information related to the concentration of carbon dioxide of gas at or near the airway of a subject. The processor is configured to execute modules, including a concentration module, a trough identification module, a plateau identification module, and a breath identification module. The concentration module is configured to determine a level of the concentration of carbon dioxide in the gas at or near the airway of the subject based on the output signals. The trough identification module is configured to identify troughs in the level of the concentration of carbon dioxide corresponding to inhalations by the subject. The plateau identification module is configured to identify plateaus in the level of the concentration of carbon dioxide corresponding to exhalations by the subject.

The breath identification module is configured to identify breaths based on identification of troughs and plateaus by the trough identification module and the plateau identification module such that responsive to identification of a trough followed by a plateau the breath identification module identifies a breath.

Another aspect of the disclosure relates to a method of detecting breaths based on capnographic information. In one embodiment, the method comprises monitoring a level of the concentration of carbon dioxide in the gas at or near the airway of the subject; identifying troughs in the level of the concentration of carbon dioxide corresponding to inhalations by the subject; identifying plateaus in the level of the concentration of carbon dioxide corresponding to exhalations by the subject; and identifying breaths based on identifications of troughs and plateaus such that responsive to identification of a trough followed by a plateau a breath is identified.

Yet another aspect of the disclosure relates to a system for detecting breaths based on capnographic information. In one embodiment, the system comprises means (28, 32) for monitoring a level of the concentration of carbon dioxide in the gas at or near the airway of the subject; means (34) for identifying troughs in the level of the concentration of carbon dioxide corresponding to inhalations by the subject; means (36) for identifying plateaus in the level of the concentration of carbon dioxide corresponding to exhalations by the subject; and means (38) for identifying breaths based on identifications of troughs and plateaus such that responsive to identification of a trough followed by a plateau a breath is identified.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment, the structural components illustrated herein are drawn to scale. It is to be expressly understood, however, that the drawings are for the purpose of illustration and description only and are not a limitation. In addition, it should be appreciated that structural features shown or described in any one embodiment herein can be used in other embodiments as well. It is to be expressly understood, however, that the drawings are for the purpose of illustration and description only and are not intended as a definition of limits. As used in the specification and in the claims, the singular form of "a", "an", and "the" include plural referents unless the context clearly dictates otherwise.

DETAILED DESCRIPTION OF THE EXEMPLARY EMBODIMENT

Figure 1:
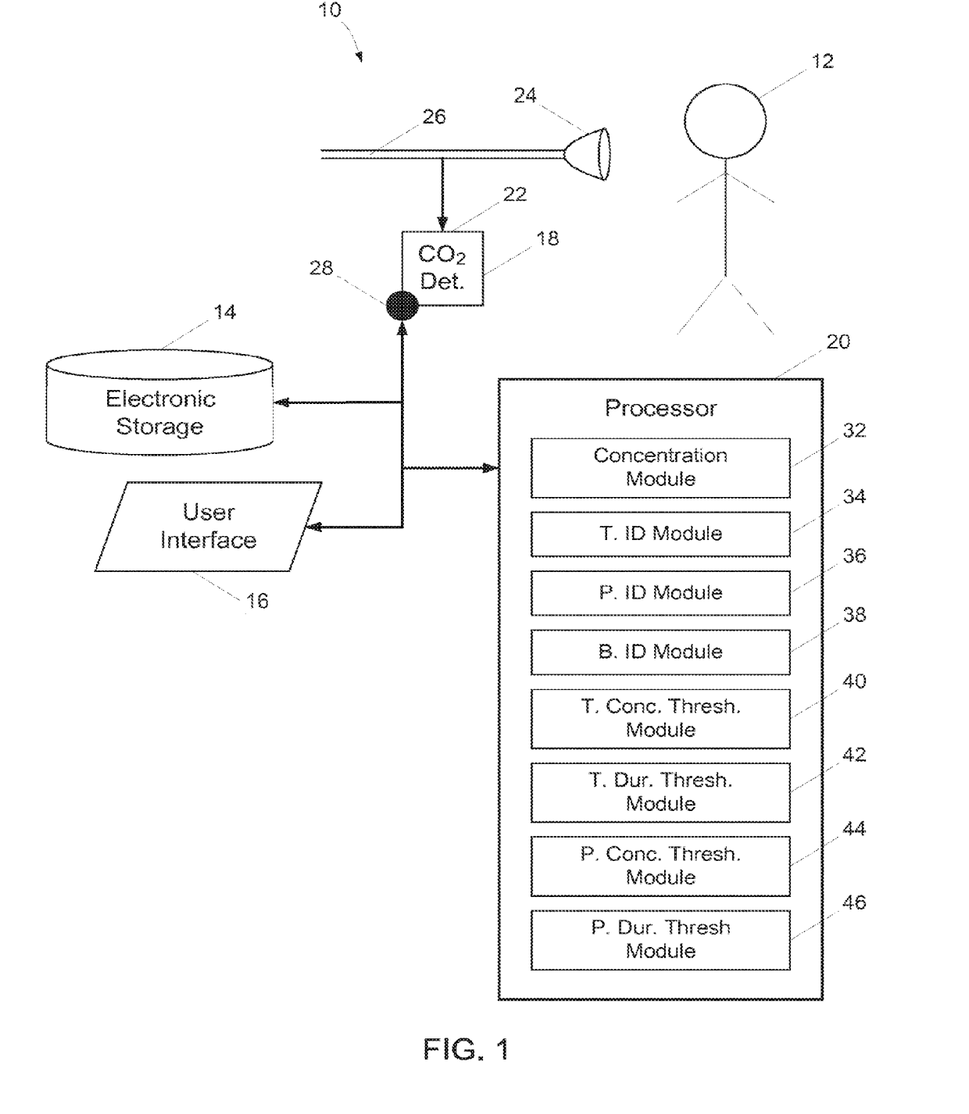
FIG. 1 illustrates a system configured to identify breaths by a subject based on information related to the concentration of a gaseous molecular species at or near the airway of the subject.

FIG. 1 illustrates a system 10 configured to identify breaths of a subject 12. In particular, system 10 is configured to identify breaths of a subject 12 based solely on information related to the concentration of a gaseous molecular species present in gas at or near the airway of subject 12. This gaseous molecular species may be carbon dioxide, as is described below. However this is not intended to be limiting, as the scope of this disclosure extends to other molecular species analyzed according to the principles described herein. In one embodiment, system 10 includes electronic storage 14, a user interface 16, a carbon dioxide detector 18, a processor 20, and/or other components.

In one embodiment, electronic storage 14 comprises electronic storage media that electronically stores information. The electronic storage media of electronic storage 14 may include one or both of system storage that is provided integrally (La, substantially non-removable) with system 10 and/or removable storage that is removably connectable to system 10 via, for example, a port (e.g., a USB port, a firewire port, etc.) or a drive (e.g., a disk drive, etc.). Electronic storage 14 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 14 may store software algorithms, information determined by processor 20, information received via user interface 16, and/or other information that enables system 10 to function properly. Electronic storage 14 may be a separate component within system 10, or electronic storage 14 may be provided integrally with one or more other components of system 10 (e.g., processor 20).

User interface 16 is configured to provide an interface between system 10 and a user (e.g., the user, a caregiver, a therapy decision-maker, etc.) through which the user may provide information to and receive information from system 10. This enables data, results, and/or instructions and any other communicable items, collectively referred to as "information," to be communicated between the user and system 10. Examples of interface devices suitable for inclusion in user interface 16 include a keypad, buttons, switches, a keyboard, knobs, levers, a display screen, a touch screen, speakers, a microphone, an indicator light, an audible alarm, and a printer.

It is to be understood that other communication techniques, either hard-wired or wireless, are also contemplated by the present invention as user interface 16. For example, the present invention contemplates that user interface 16 may be integrated with a removable storage interface provided by electronic storage 14. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 16 include, but are not limited to, an RS-232 port, RF link, an IR link, modem (telephone, cable or other). In short, any technique for communicating information with system 10 is contemplated by the present invention as user interface 16.

The carbon dioxide detector 18 is configured to obtain gas from at or near the airway of subject 12, and to generate output signals conveying information obtained from measurements taken from the obtained gas. The carbon dioxide detector 18 is configured to receive gas obtained at or near the airway of subject 12 via an inlet 22. The gas is conveyed to inlet 22 by way of a subject interface appliance 24 and/or a conduit 26. The subject interface appliance 24 may engage one or more orifices of the airway of subject 12 in a sealed or unsealed manner. Some examples of subject interface appliance 24 may include, for example, an endotracheal tube, a nasal cannula, a tracheotomy tube, a nasal mask, a nasal/oral mask, a full face mask, a total face mask, a partial rebreathing mask, or other interface appliances that communicate a flow of gas with an airway of a subject. The present invention is not limited to these examples, and contemplates implementation of any subject interface.

The conduit 26 is configured to place inlet 22 of carbon dioxide detector 18 in fluid communication with subject interface appliance 24 such that gas obtained by subject interface appliance 24 from at or near the airway of subject 12 is provided to inlet 22 via conduit 26. In one embodiment, carbon dioxide detector 18 is configured for sidestream sampling. In this configuration, conduit 26 is further configured to place subject interface appliance 24 in fluid communication with a source of a breathable substance. For example, a flow of breathable gas may be delivered to subject 12 through conduit 26 having one or more parameters that are controlled in accordance with a therapy regime. The one or more parameters of the flow of breathable gas that are controlled may include one or more of pressure, flow, composition, humidity, temperature, and/or other parameters. In one embodiment, carbon dioxide detector 18 is configured for mainstream sampling. In this configuration, carbon dioxide detector 18 is disposed within the flow path through conduit 26, rather than being disposed off to the side (as is shown in FIG. 1). In one embodiment in which carbon dioxide detector 18 configured for sidestream sampling, or in which conduit 26 does not provide for provision of a breathable substance to the airway of subject 12, a pump (not shown) is configured to draw gas from conduit 26 into carbon dioxide detector 18 through inlet 22.

The carbon dioxide detector 18 includes a carbon dioxide sensor 28. The carbon dioxide sensor 28 is configured to generate output signals conveying information related to the concentration of carbon dioxide in the gas within carbon dioxide detector 18. It will be appreciated that the illustration of carbon dioxide sensor 28 in FIG. 1 the only sensor within carbon dioxide detector 18 is not intended to be limiting. In one embodiment, carbon dioxide detector 18 includes a plurality of sensors. The plurality of sensor may be configured to monitor other parameters of the gas received into carbon dioxide detector 18. The other parameters may include one or more of pressure, flow, composition, humidity, temperature, and/or other parameters.

Processor 20 is configured to provide information processing capabilities in system 10. As such, processor 20 may include one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 may include a plurality of processing units. These processing units may be physically located within the same device, or processor 20 may represent processing functionality of a plurality of devices operating in coordination.

As is shown in FIG. 1, processor 20 may be configured to execute one or more computer program modules. The one or more computer program modules may include one or more of a concentration module 32, a trough identification module 34, a plateau identification module 36, a breath identification module 38, a trough concentration threshold module 40, a trough duration threshold module 42, a plateau concentration threshold module 44, a plateau duration threshold module 46, and/or other modules. Processor 20 may be configured to execute modules 32, 34, 36, 38, 40, 42, 44, and/or 46 by software; hardware; firmware; some combination of software, hardware, and/or firmware; and/or other mechanisms for configuring processing capabilities on processor 20.

It should be appreciated that although modules 32, 34, 36, 38, 40, 42, 44, and 46 are illustrated in FIG. 1 as being co-located within a single processing unit, in implementations in which processor 20 includes multiple processing units, one or more of modules 32, 34, 36, 38, 40, 42, 44, and/or 46 may be located remotely from the other modules. The description of the functionality provided by the different modules 32, 34, 36, 38, 40, 42, 44, and/or 46 described below is for illustrative purposes, and is not intended to be limiting, as any of modules 32, 34, 36, 38, 40, 42, 44, and/or 46 may provide more or less functionality than is described. For example, one or more of modules 32, 34, 36, 38, 40, 42, 44, and/or 46 may be eliminated, and some or all of its functionality may be provided by other ones of modules 32, 34, 36, 38, 40, 42, 44, and/or 46.

As another example, processor 20 may be configured to execute one or more additional modules that may perform some or all of the functionality attributed below to one of modules 32, 34, 36, 38, 40, 42, 44, and/or 46.

Figure 2:
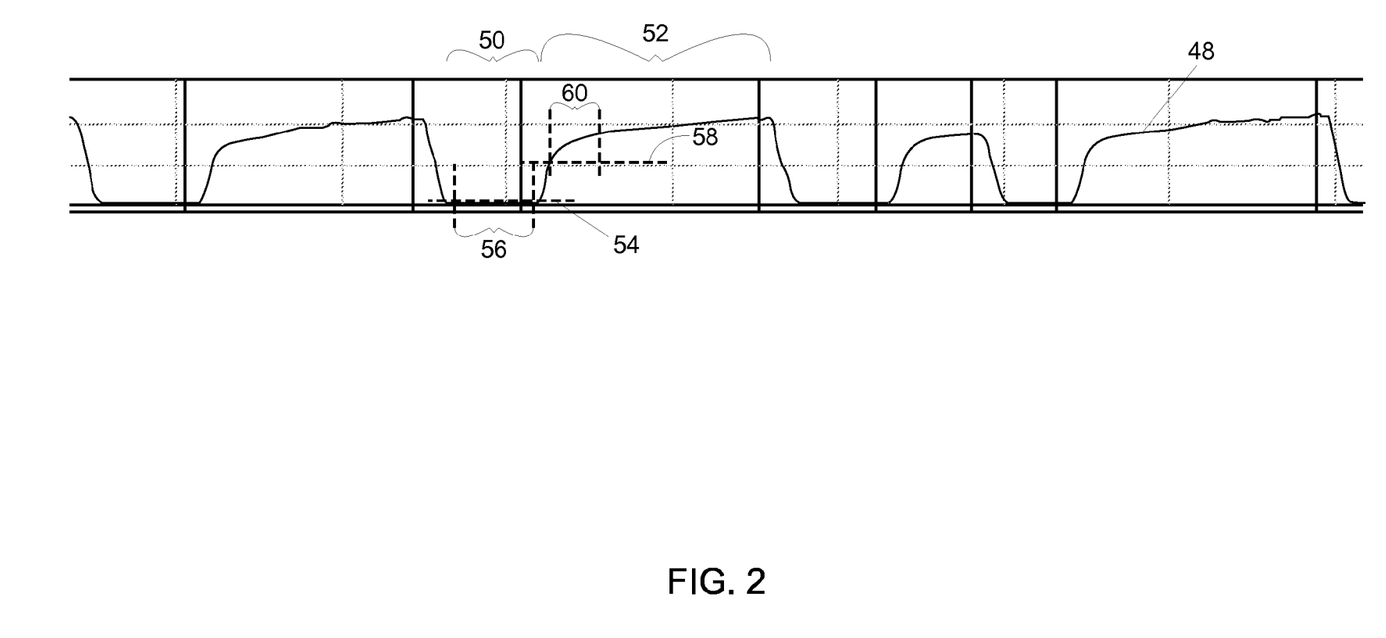
FIG. 2 illustrates a plot of concentration of carbon dioxide at or near the airway of a subject versus time.

The concentration module 32 is configured to determine a level of the concentration of carbon dioxide in the gas at or near the airway of subject 12. The concentration module 32 to make this determination based on the output signals generated by carbon dioxide sensor 28. By way of illustration, FIG. 2 depicts a plot 48 of carbon dioxide concentration versus time as a subject breathes. As can be seen in FIG. 2, plot 48 respiration by the subject results in troughs, such as trough 50, and plateaus, such as plateau 52, in the level of carbon dioxide concentration. The troughs are characterized by a plot of carbon dioxide that is horizontal at a minimum level. The plateaus are characterized by a plot of carbon dioxide that is elevated from the minimum level with a slight increase over time to a maximum at the conclusion of exhalation. Conventional systems for determining breath rate from capnographic data typically identify breaths simply as dips from the plateau level. However, this technique may lead to false positives (e.g., over counting breath rate), due to flow artifacts caused by cardiogenic oscillations and other ineffective gas movements the breathing circuit.

Returning to FIG. 1, the trough identification module 34 is configured to identify troughs in the level of carbon dioxide at or near the airway of subject 12 that correspond to inhalations by subject 12. The trough identification module 34 is configured such that a trough is identified responsive to the level of the concentration of carbon dioxide falling below a trough concentration threshold for an amount of time greater than a through duration threshold. Turning back to FIG. 2, the plot 48 is demarcated with a trough concentration threshold 54 and a trough duration threshold 56. Referring again to FIG. 1, the trough identification module 34 compares the concentration of carbon dioxide determined by concentration module 32 with the trough concentration threshold until the concentration of carbon dioxide falls below the trough concentration threshold. Once the concentration of carbon dioxide is below the trough concentration threshold, the trough identification module 34 monitors a time the concentration is maintained below the trough concentration threshold. Responsive to this time exceeding the trough duration threshold, trough identification module 34 identifies a trough corresponding to inhalation by subject 12.

In one embodiment, trough identification module 34 is configured such that in addition to requiring satisfaction of the trough concentration threshold and the trough duration threshold, trough identification module 34 also requires the level of carbon dioxide during the trough to remain flat over the amount of time corresponding to the trough duration threshold. For example, responsive to satisfaction of the trough concentration threshold and the trough duration threshold, trough identification module 34 identifies a potential trough, and compares a level of carbon dioxide at the beginning of the potential trough with the level of carbon dioxide at the end of the potential trough. Responsive to a difference between the level at the beginning of the potential trough and the level of carbon dioxide at the end of the potential trough being less than a trough differential threshold, trough identification module 34 identifies the potential trough as a trough corresponding to inhalation. The trough differential threshold may be a predetermined value, a user-configurable value, a dynamically determined, value, and/or may be derived through other means. In one embodiment, the trough differential threshold is about 3 mm Hg.

The plateau identification module 36 is configured to identify plateaus in the level of the concentration of carbon dioxide at or near the airway of subject 12 that correspond to exhalations by subject 12. The plateau identification module 36 is configured such that a plateau is identified responsive to the level of carbon dioxide rising above a plateau concentration threshold for an amount of time greater than a plateau duration threshold. In one embodiment, plateau identification module 36 is configured such that a sustained elevation of the concentration of carbon dioxide is only identified as a plateau if the concentration exceeded the plateau concentration threshold within a specific amount of time of a trough identified by trough identification module 34. In other words, the first criteria for identifying a plateau may be the identification of a preceding trough by trough identification module 34.

Turning back to FIG. 2, the plot 48 is demarcated with a plateau concentration threshold 58 and a plateau duration threshold 60. Referring again to FIG. 1, the plateau identification module 36 compares the concentration of carbon dioxide concentration determined by concentration module 32 with the plateau concentration threshold until the concentration of carbon dioxide rises above the plateau concentration threshold. Once the concentration of carbon dioxide is above the plateau concentration threshold, the plateau identification module 36 monitors a time the concentration is maintained above the plateau concentration threshold. Responsive to this time exceeding the plateau duration threshold, plateau identification module 36 identifies a plateau corresponding to exhalation by subject 12.

The breath identification module 38 is configured to identify breaths by subject 12. The breath identification module 38 is configured such that responsive to identification of a trough by trough identification module 34 being followed by identification of a plateau by plateau identification module 36 a breath is identified. This analysis includes a robust identification of each of inhalation and exhalation, and/or requires an identified inhalation (or trough) to be followed by an identified exhalation (or plateau) before identifying a breath. The identifications of breaths can be used by a breath rate module (not shown) configured to determine one or more breathing parameters of subject 12. The breathing parameters may include breath rate, apnea time, inspiratory time, expiratory time, I:E ratio, end-tidal CO2, and/or other breathing parameters.

The trough concentration threshold module 40 is configured to determine the trough concentration threshold used by trough identification module 34. The trough concentration threshold module 40 is configured to determine the trough concentration threshold dynamically based on respiration of subject 12. In one embodiment, trough concentration threshold module 40 determines the magnitude of the through concentration threshold to be the lowest CO2 level observed during a prior sliding window of time (e.g., the previous minute) plus some offset value (e.g., about 4 mm Hg). This dynamic determination of the trough concentration threshold may account for drift in the generation of the output signals by carbon dioxide sensor 28. In one embodiment, a maximum value is set for the trough concentration threshold. This may be set at manufacture, by user configuration, and/or otherwise set. If the trough concentration threshold determined by trough concentration threshold module 40 dynamically based on respiration of subject 12 exceeds the maximum, then trough concentration threshold module 40 implements the maximum as the trough concentration threshold. In one embodiment, the maximum trough concentration threshold is about 10 mm Hg.

The trough duration threshold module 42 is configured to determine the trough duration threshold used by trough identification module 34. The trough duration module 42 is configured to determine the trough concentration threshold dynamically based on respiration of subject 12. In one embodiment, trough duration threshold module 42 is configured to determine the trough duration threshold for a given breath n as the average trough duration less the standard deviation of the trough duration of the breaths detected during the period immediately prior to the time of the given breath n (e.g., over breaths n−m through n−1). In this embodiment, trough duration module 42 may be configured to determine the average and standard deviation using an algorithm that calculates a time weighted average of the most recent values where the most recent breath n−1 is the most heavily weighted and prior breath data is given less weight. Weighting of older data decreases exponentially with decreasing value given to older breaths. One non-limiting example of such an algorithm is:

$$(1) Y[n] = \alpha * Y[n-1] + (1-\alpha) * X[n];$$

where $Y[n]$ represents the new average value; $Y[n-1]$ represents the previous average; $\alpha$ represents a factor between 0 and 1.0 (larger value of $\alpha$ gives a longer average); and $X[n]$ represents a new sample.

The trough duration module 42 is configured to determine the standard deviation of the trough duration as the square root of the time weighted variance. The variance is calculated similarly as the average where the input (new sample or $X[n]$) is the squared difference between the new data point and the weighted average value. This is represented as:

$$(2) Var[n] = \alpha * Var[n-1] + (1-\alpha) * (X[n] - Y[n])^2;$$

where $Var[n]$ represents the new variance, and $Var[n-1]$ represents the previous variance.

The trough duration module 42 may be configured such that the determined trough duration and/or the variance may be compared with limits. The limits may include upper and/or lower limits. If a determined trough duration threshold and/or variance breaches a limit, the trough duration module 42 may be configured to implement a previously determined trough duration threshold and/or variance, implement the exceeded limit, and/or implement some other value.

The plateau concentration module 44 is configured to determine the plateau concentration threshold used by plateau identification module 36. The plateau concentration module 44 is configured to determine the plateau concentration threshold dynamically based on respiration of subject 12. In one embodiment, plateau concentration module 44 is configured to determine the plateau concentration threshold as 50% (or some other proportion) of the average maximum concentration of carbon dioxide (end-tidal carbon dioxide) observed during previously detected breaths. The average maximum concentration of carbon dioxide value is calculated as a time-weighted average as described above for trough duration where the value for $\alpha=0.75$ (faster changes) if the new maximum breath carbon dioxide concentration is greater than the present average and $\alpha=0.925$ if the new maximum carbon dioxide concentration value is less than the present average. This logic allows the threshold value to rise more quickly than it falls. Since new higher end-tidal carbon dioxide concentration values generally reflect an actual physiologic change and lower than average end-tidal carbon dioxide concentration values often reflect artifact (smaller tidal volume than airway dead volume), the average is allowed to change upward quickly and is more cautious toward decreasing the average.

The plateau concentration module 44 is configured to compare the determined average end-tidal carbon dioxide concentration and/or the plateau concentration threshold with one or more limits (e.g., upper and/or lower). The limit(s) may be configured at manufacture, configured by a user, and/or otherwise determined or configured. If the determined average end-tidal carbon dioxide concentration and/or the plateau concentration threshold breaches a limit, plateau concentration module 44 may implement the limit, a previously determined average end-tidal carbon dioxide concentration and/or plateau concentration threshold, or some other value.

The plateau duration module 46 is configured to determine the plateau duration threshold. In one embodiment plateau duration module is configured to determine the plateau duration threshold as 10% (or some other proportion) of the time-weighted average breath duration of subject 12. The time-weighted average breath duration may be determined similar to the determination of time-weighted average trough duration set forth above where $\alpha$ is set at 0.9.

The plateau duration module 46 is configured to compare the determined average breath time and/or the plateau duration threshold with one or more limits (e.g., upper and/or lower). The limit(s) may be configured at manufacture, configured by a user, and/or otherwise determined or configured. If the determined average breath time and/or the plateau duration threshold breaches a limit, plateau duration module 46 may implement the limit, a previously determined average breath time and/or plateau duration threshold, or some other value.

In one embodiment, modules 40, 42, 44, and/or 46 are configured to reset their respective thresholds. Since the thresholds are statistically determined based on the breaths detected immediately prior, there is a chance that when there is a sudden change in the signal that legitimate breaths will not be detected. One or more of modules 40, 42, 44, and/or 46 may be configured to execute a "soft reset" if a breath is not detected within an expected time limit. In one embodiment, the expected time limit is calculated as the average breath duration plus three times the standard deviation of the breath duration. The average breath duration and the variance of the breath duration are calculated as described above. This logic means that when breath timing is very regular, that the threshold is set slightly above the average breath duration. Alternatively, when breath duration is variable, then the time before a soft reset is executed is extended.

In a soft reset, all of the detection thresholds are reduced so that breath detection is more likely. The trough duration threshold module 42 may be configured to set the trough duration threshold to 60% (or some other proportion) of the prior value. The breath detection threshold may be set to 80% (or some other proportion) of its prior value. The same minimum and maximum limits on these values that are applied when they are normally calculated are applied when they are modified during a soft reset. In a soft reset, the average values that are used to calculate the thresholds are reduced by the same percentage as the thresholds are reduced. Without reduction of the average values, then the thresholds would increase to their pre-reset values on the subsequent breath detection.

Figure 3:
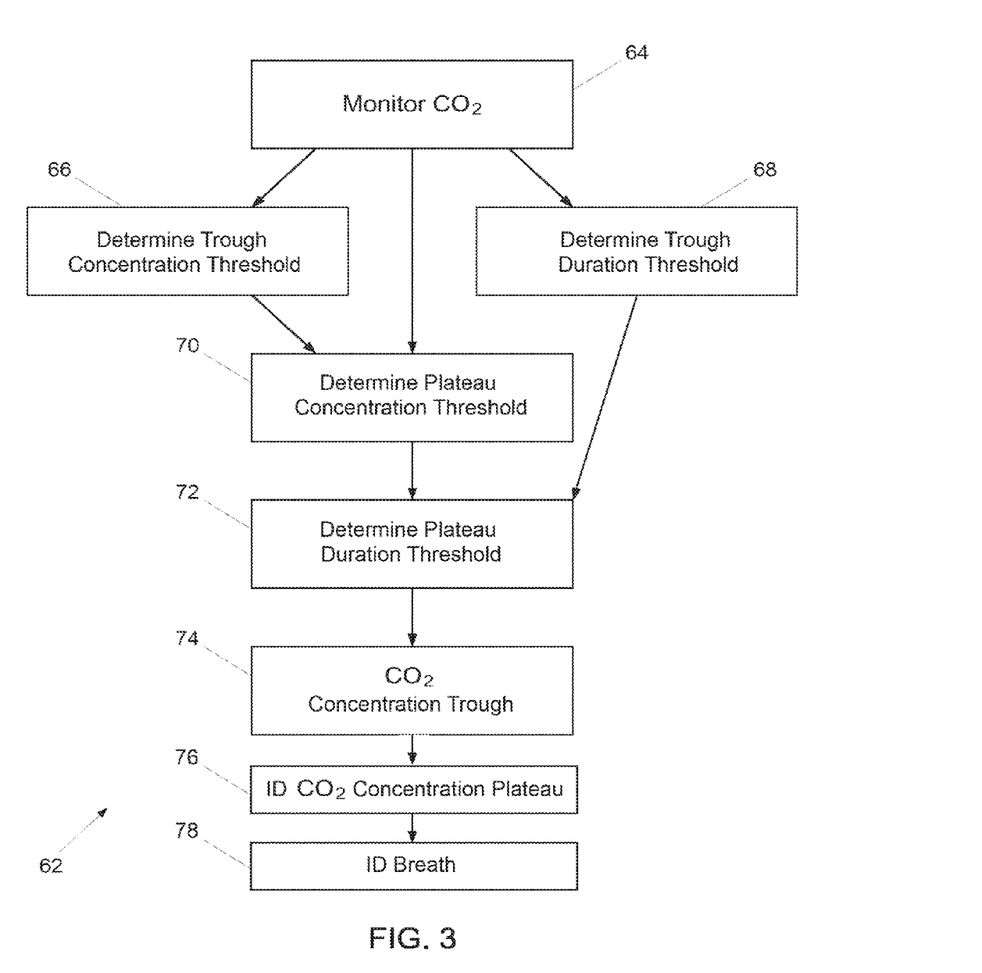
FIG. 3 illustrates a method of identifying breaths of a subject.

FIG. 3 illustrates a method 62 of detecting breaths based on capnographic information. The operations of method 62 presented below are intended to be illustrative. In some embodiments, method 62 may be accomplished with one or more additional operations not described, and/or without one or more of the operations discussed. Additionally, the order in which the operations of method 62 are illustrated in FIG. 3 and described below is not intended to be limiting.

In some embodiments, method 62 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 62 in response to instructions stored electronically on an electronic storage medium. The one or more processing devices may include one or more devices configured through hardware, firmware, and/or software to be specifically designed for execution of one or more of the operations of method 62.

At an operation 64, a level of the concentration of carbon dioxide in the gas at or near the airway of the subject is monitored. This may include sampling the concentration of carbon dioxide in gas obtained at or near the airway of the subject. In one embodiment, operation 64 is performed by a carbon dioxide sensor and concentration module similar to or the same as carbon dioxide sensor 28 and concentration module 32 (shown in FIG. 1 and described above).

At an operation 66, a trough concentration threshold is determined. The trough concentration threshold is determined based on breathing of the subject (e.g., based on the level of concentration determined at operation 64 during past breaths). In one embodiment, operation 66 is performed by a trough concentration threshold module the same as or similar to trough concentration threshold module 40 (shown in FIG. 1 and described above).

At an operation 68, a trough duration threshold is determined. The trough duration threshold is determined based on breathing of the subject (e.g., based on the level of concentration determined at operation 64 during past breaths). In one embodiment, operation 68 is performed by a trough duration threshold module the same as or similar to trough duration threshold module 42 (shown in FIG. 1 and described above).

At an operation 70, a plateau concentration threshold is determined. The plateau concentration threshold is determined based on breathing of the subject (e.g., based on the level of concentration determined at operation 64 during past breaths). In one embodiment, operation 70 is performed by a plateau concentration threshold module the same as or similar to plateau concentration threshold module 44 (shown in FIG. 1 and described above).

At an operation 72, a plateau duration threshold is determined. The plateau duration threshold is determined based on breathing of the subject (e.g., based on the level of concentration determined at operation 64 during past breaths). In one embodiment, operation 72 is performed by a plateau duration threshold module the sameas or similar to plateau duration threshold module 40 (shown in FIG. 1 and described above).

At an operation 74, a trough in the concentration of carbon dioxide is identified. The trough corresponds to an inhalation by the subject. The trough is identified responsive to the level of the concentration of carbon dioxide falling below a trough concentration threshold for an amount of time greater than a trough duration threshold. In one embodiment, operation 74 is performed by a trough identification module the same as or similar to trough identification module 34 (shown in FIG. 1 and described above).

At an operation 76, a plateau in the concentration of carbon dioxide is identified. The plateau corresponds to an exhalation by the subject. The plateau is identified responsive to the level of carbon dioxide rising above a plateau concentration threshold for an amount of time greater than a plateau duration threshold. In one embodiment, operation 76 is performed by a plateau identification module the same as or similar to plateau identification module 36 (shown in FIG. 1 and described above).

At an operation 78, a breath is identified. The breath is identified responsive to the identification of the trough being followed by the identification of the plateau. In one embodiment, operation 78 is performed by a breath identification module the same as or similar to breath identification module 38 (shown in FIG. 1 and described above).

Details included herein are for the purpose of illustration based on what is currently considered to be the most practical and preferred embodiments, it is to be understood that such detail is solely for that purpose and that the scope of this specification is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to detect breaths based on capnographic information, the system comprising:
    one or more carbon dioxide sensors configured to generate output signals over time conveying information related to a concentration of carbon dioxide in gas at or near the airway of a subject;
    one or more digital processors configured to execute instructions stored on an electronic storage medium to:
        determine a level of the concentration of carbon dioxide in the gas at or near the airway of the subject over time based on the output signals;
        identify troughs in the determined level of the concentration of carbon dioxide, via satisfaction per trough of a trough concentration threshold and a trough duration threshold over time, corresponding to inhalations by the subject,
        identify a potential trough via a comparison of a level of carbon dioxide at a beginning of the potential trough with a level of carbon dioxide at an end of the same potential trough, wherein responsive to a difference between (i) the level at the beginning of the potential trough and (ii) the level of carbon dioxide at the end of the same potential trough being less than a trough differential threshold, the potential trough being identified as a trough corresponding to an inhalation;
        identify plateaus in the determined level of the concentration of carbon dioxide over time corresponding to exhalations by the subject; and
        identify breaths based on identification of troughs and plateaus over time wherein responsive to (i) an identification of a trough followed by (ii) an identification of a plateau, identifying a breath;

determine one or more breathing parameters of the subject including one or more of breath rate, apnea time, inspiratory time, expiratory time, I:E ratio, and end-tidal $CO_2$; and communicating the determined breathing parameters of the subject via a user interface.

2. The system of claim 1, wherein the trough is identified responsive to the level of the concentration of carbon dioxide falling below the trough concentration threshold for an amount of time greater than the trough duration threshold.

3. The system of claim 2, wherein the one or more digital processors are configured to execute the instructions stored on the electronic storage medium to further dynamically determine the trough concentration threshold based on previous respiration of the subject by adding a predetermined offset value to a lowest carbon dioxide level determined during a prior sliding window of time.

4. The system of claim 2, wherein the one or more digital processors are configured to execute the instructions stored on the electronic storage medium to further dynamically determine the trough duration threshold for a given breath based on respiration of the subject by subtracting a standard deviation of one or more breaths detected during a period immediately prior to a time of the given breath from an average trough duration.

5. The system of claim 1, wherein the plateau is identified subsequent to identification of a trough responsive to the level of carbon dioxide rising above a plateau concentration threshold for an amount of time greater than a plateau duration threshold.

6. The system of claim 5, wherein the one or more digital processors are configured to execute the instructions stored on the electronic storage medium to further dynamically determine, based on previous respiration of the subject, the plateau concentration threshold as a predetermined proportion of an average maximum concentration of carbon dioxide.

7. The system of claim 5, wherein the one or more digital processors are configured to execute the instructions stored on the electronic storage medium to further dynamically determine, based on previous respiration of the subject, the plateau duration threshold as a predetermined proportion of a time-weighted average breath duration.

8. The system of claim 1, wherein the one or more digital processors are configured to execute the instructions stored on the electronic storage medium to determine the one or more breathing parameters solely based on the output signals over time conveying information related to a concentration of carbon dioxide in gas at or near the airway of a subject.

9. A method of detecting breaths based on capnographic information, the method comprising:

monitoring over time, by one or more sensors, a level of the concentration of carbon dioxide in gas at or near the airway of the subject;

identifying troughs, by one or more processors, in the level of the concentration of carbon dioxide, via satisfaction per trough of a trough concentration threshold and a trough duration threshold over time, corresponding to inhalations by the subject, wherein identifying further includes identifying a potential trough via a comparison of a level of carbon dioxide at a beginning of the potential trough with a level of carbon dioxide at an end of the same potential rough, wherein responsive to a difference between (i) the level at the beginning of the potential trough and (ii) the level of carbon dioxide at the end of the same potential trough being less than a trough differential threshold, the potential trough is identified as a trough corresponding to an inhalation;

identifying plateaus, by the one or more processors, in the level of the concentration of carbon dioxide over time corresponding to exhalations by the subject;

identifying breaths, by the one or more processors, based on identifications of troughs and plateaus, wherein responsive to (i) an identification of a trough followed by (ii) an identification of a plateau, a breath is identified; and communicating the identified breaths to the subject via a user interface.

10. The method of claim 9, wherein identifying troughs comprises identifying a trough corresponding to an inhalation by the subject responsive to the level of the concentration of carbon dioxide falling below the trough concentration threshold for an amount of time greater than the trough duration threshold.

11. The method of claim 10, further comprising dynamically determining the trough concentration threshold based on respiration of the subject by adding a predetermined offset value to a lowest carbon dioxide level determined during a prior sliding window of time.

12. The method of claim 10, further comprising dynamically determining the trough duration threshold for a given breath based on respiration of the subject by subtracting a standard deviation of one or more breaths detected during a period immediately prior to a time of the given breath from an average trough duration.

13. The method of claim 9, wherein identifying plateaus comprises identifying a plateau corresponding to an exhalation by the subject subsequent to identification of a trough responsive to the level of carbon dioxide rising above a plateau concentration threshold for an amount of time greater than a plateau duration threshold.

14. The method of claim 13, further comprising dynamically determining, based on respiration of the subject, the plateau concentration threshold as a predetermined proportion of an average maximum concentration of carbon dioxide.

15. The method of claim 13, further comprising dynamically determining, based on previous respiration of the subject, the plateau duration threshold as a predetermined proportion of a time-weighted average breath duration.

16. A system for detecting breaths based on capnographic information, the system comprising:

means for monitoring a level of the concentration of carbon dioxide in gas at or near the airway of the subject over time;

means for identifying troughs in the level of the concentration of carbon dioxide, via satisfaction per trough of a trough concentration threshold and a trough duration threshold over time corresponding to inhalations by the subject, wherein the troughs identifying means is further configured to identity a potential trough via a comparison of a level of carbon dioxide at a beginning of the potential trough with a level of carbon dioxide at an end of the same potential trough, wherein responsive to a difference between (i) the level at the beginning of the potential trough and (ii) the level of carbon dioxide at the end of the same potential trough being less than a trough differential threshold, the troughs identifying means identifies the potential trough as a trough corresponding to an inhalation;

means for identifying plateaus in the level of the concentration of carbon dioxide over time corresponding to exhalations by the subject;

means for identifying breaths based on identifications of troughs and plateaus over time, wherein responsive to (i) an identification of a trough by the trough identifying means, followed by (ii) an identification of a plateau by the plateaus identifying means, the breaths identifying means identifies a breath; and means for communicating the identified breaths to the subject.

17. The system of claim 16, wherein the means for identifying troughs identifies a trough corresponding to an inhalation by the subject responsive to the level of the concentration of carbon dioxide falling below the trough concentration threshold for an amount of time greater than the trough duration threshold.

18. The system of claim 17, further comprising means for dynamically determining, based on respiration of the subject, both of the trough concentration threshold and the trough duration threshold based on respiration of the subject;

wherein the trough concentration threshold is determined by adding a predetermined offset value to a lowest carbon dioxide level determined during a prior sliding window of time; and wherein the trough duration threshold for a given breath is determined by subtracting a standard deviation of one or more breaths detected during a period immediately prior to a time of the given breath from an average trough duration.

19. The system of claim 16, wherein the means for identifying plateaus identifies a plateau corresponding to an exhalation by the subject subsequent to identification of a trough responsive to the level of carbon dioxide rising above a plateau concentration threshold for an amount of time greater than a plateau duration threshold.

20. The system of claim 19, further comprising means for dynamically determining both of the plateau concentration threshold and the plateau duration threshold based on respiration of the subject;

wherein the plateau concentration threshold is determined as a predetermined proportion of an average maximum concentration of carbon dioxide: and wherein the plateau duration threshold is determined as a predetermined proportion of a time-weighted average breath duration.

* * * * *